US012599214B2

(12) United States Patent (10) Patent No.: US 12,599,214 B2
Knapp (45) Date of Patent: Apr. 14, 2026

(54) ITCH PICK DEVICE

(71) Applicant: Kareen Knapp, St. Petersburg, FL (US)

(72) Inventor: Kareen Knapp, St. Petersburg, FL (US)

( * ) Notice: Subject to any disclaimer, the term of this patent is extended or adjusted under 35 U.S.C. 154(b) by 343 days.

(21) Appl. No.: 18/353,329

(22) Filed: Jul. 17, 2023

(65) Prior Publication Data

US 2024/0023690 A1     Jan. 25, 2024

Related U.S. Application Data

(60) Provisional application No. 63/390,472, filed on Jul. 19, 2022.

(51) Int. Cl.
*A45D 24/02* (2006.01)
*A45D 24/22* (2006.01)
*A61M 35/00* (2006.01)

(52) U.S. Cl.
CPC ............. *A45D 24/02* (2013.01); *A45D 24/22* (2013.01); *A61M 35/003* (2013.01)

(58) Field of Classification Search
CPC .. A45D 24/02; A45D 24/22; A45D 2034/007; A45D 34/00; A61M 35/003
See application file for complete search history.

(56) References Cited

U.S. PATENT DOCUMENTS

| | | | |
|---|---|---|---|
| 3,768,463 A | 10/1973 | Curry | |
| D481,168 S | 10/2003 | Shannon | |
| 8,997,756 B2 | 4/2015 | Haynes | |
| D836,250 S | 12/2018 | Rice | |
| 12,256,821 B1 * | 3/2025 | Garey | A45D 34/042 |
| 2011/0245811 A1 | 10/2011 | Sabal | |
| 2012/0121313 A1 | 5/2012 | Thiebaut | |
| 2016/0339221 A1 * | 11/2016 | Patterson | A61H 7/003 |
| 2019/0289992 A1 * | 9/2019 | Thiruppathi | A46B 11/0055 |
| 2020/0086097 A1 * | 3/2020 | Lao | B65D 83/303 |
| 2021/0137258 A1 * | 5/2021 | Tam | A46B 15/0022 |
| 2022/0362528 A1 * | 11/2022 | Williams | A45D 34/04 |

* cited by examiner

*Primary Examiner* — Susan S Su

(74) *Attorney, Agent, or Firm* — Brennan, Manna & Diamond, LLC

(57) ABSTRACT

A hair pick device is disclosed that provides itch relief to a user's scalp while he/she is wearing different hairstyles. The device is a pick-like tool with the ability to maneuver through hairdos including dreads, braids, weaves, and wigs to scratch the scalp without ruining the hairstyle. The hair pick device comprises a body component that is configured in a cylindrical shape that may be solid or hollow. If hollow, the body component would also comprise a chamber, allowing the user to insert conditioners or other moisturizers into the device for application to the head. Further, the body component comprises an end component tapered into a point. The end component can be retractable or the device can be a single unitary piece.

16 Claims, 4 Drawing Sheets

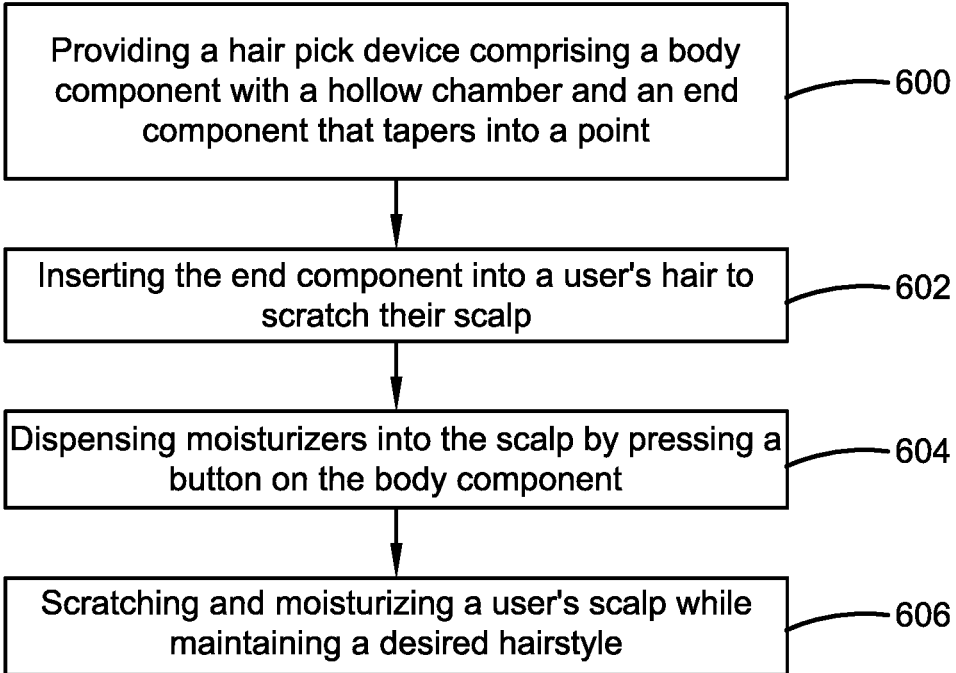

Providing a hair pick device comprising a body component with a hollow chamber and an end component that tapers into a point — 600

Inserting the end component into a user's hair to scratch their scalp — 602

Dispensing moisturizers into the scalp by pressing a button on the body component — 604

Scratching and moisturizing a user's scalp while maintaining a desired hairstyle — 606

FIG. 6

ITCH PICK DEVICE

CROSS-REFERENCE TO RELATED APPLICATION

The present application claims priority to, and the benefit of, U.S. Provisional Application No. 63/390,472, which was filed on Jul. 19, 2022, and is incorporated herein by reference in its entirety.

FIELD OF THE INVENTION

The present invention relates generally to the field of hair pick devices. More specifically, the present invention relates to a pick-like tool for itching the scalp while wearing a wig, weave, dreadlocks, and other hairstyles. Accordingly, this disclosure makes specific reference thereto the present invention. Nonetheless, it is to be appreciated that aspects of the present invention are also equally applicable to other like applications, devices and methods of manufacture.

BACKGROUND

By way of background, this invention relates to improvements in hair pick devices. Generally, people with specific hairstyles like dreadlocks, braids, weaves, wigs, etc., may have trouble itching and moisturizing their scalp. Further, trying to use fingernails or other tools to scratch the scalp can move hair out of place, ultimately ruining the hairstyle. Damaging the hairstyle can require expensive visits to a salon. Additionally, without moisturizing the scalp, people may develop an itchy head and/or dandruff.

Typical methods of applying a liquid directly to the scalp is to spray the liquid onto the desired area of scalp and rub it in with one's hands, or dispense the liquid directly into one's hands. However, this method is often messy and inconvenient. Further, liquid can run off of the scalp before it can be rubbed into the scalp by the person's hands. It is thus desired, to provide a device that applies a liquid directly to the hair or the scalp. It is also desirable that such a device fits into a conventional hair pick.

Accordingly, there is a demand for an improved hair pick device that allows a user to itch their scalp without damaging a hairstyle, such as dreadlocks, braids, weaves, wigs, etc. More particularly, there is a demand for a hair pick device that allows a user to moisturize their scalp via applying liquid from the hair pick device directly into the scalp.

Therefore, there exists a long felt need in the art for a hair pick device that provides users with a pick-like tool for itching the scalp while wearing a wig, weave, dreadlocks, and other hairstyles. There is also a long felt need in the art for a hair pick device that allows users to itch the scalp without destroying the hairstyle and need to spend money at a salon to have it fixed. Further, there is a long felt need in the art for a hair pick device that features a hollow interior that can store moisturizer, allowing users to release the liquid through the tip via a small button on the pick. Moreover, there is a long felt need in the art for a device that enables users to both scratch itches and moisturize their scalp, all without ruining their hairstyle. Further, there is a long felt need in the art for a hair pick device that is retractable in length. Finally, there is a long felt need in the art for a hair pick device that comprises a solid shaft, without a chamber.

The subject matter disclosed and claimed herein, in one embodiment thereof, comprises a hair pick device. The device provides itch relief to a user's scalp while he/she is wearing different hairstyles. The device is a pick-like tool with the ability to maneuver through hairdos including dreads, braids, weaves, and wigs to scratch the scalp without ruining the hairstyle. The hair pick device comprises a body component that is configured in a cylindrical shape that may be solid or hollow. If hollow, the body component would also comprise a chamber, allowing the user to insert conditioners or other moisturizers into the device for application to the head. The conditions and moisturizers would be released via a button on the side of the body component. Further, the body component comprises an end component tapered into a point. The end component can be retractable or the device can be a single unitary piece. Thus, users can scratch itches and moisturize their scalp with the pick end component without messing up their hairstyle.

In this manner, the hair pick device of the present invention accomplishes all of the forgoing objectives and provides users with a device that provides itch relief without worry of messy up a hairstyle. The device is a pick-like tool that can also comprise liquid. The device can itch and moisturize simultaneously.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a hair pick device. The device provides itch relief to a user's scalp while he/she is wearing different hairstyles. The device is a pick-like tool with the ability to maneuver through hairdos including dreads, braids, weaves, and wigs to scratch the scalp without ruining the hairstyle. The hair pick device comprises a body component that is configured in a cylindrical shape with a chamber for dispensing moisturizing liquids. Further, the body component comprises an end component tapered into a point. Thus, users can scratch itches and moisturize their scalp with the pick end component without messing up their hairstyle.

In one embodiment, the hair pick device is adapted to be used as a pick to scratch a user's scalp in order to conveniently and painlessly itch a user's scalp without disturbing a user's hairstyle. This is especially useful when a user's hairdo includes braids, dreadlocks, weaves, wigs, etc., or any other suitable hairstyle as is known in the art.

In one embodiment, the hair pick device comprises a body component manufactured from a suitable plastic, metal, wood, or other rigid material. The body component comprises a closed end, an opposing open end, and a body section. The closed end, opposing open end and body section fit together tightly to form the body component. The body component then has a substantially solid appearance that substantially approximates the appearance of a conventional hair pick. The body component is substantially cylindrical in shape and comprises a circular cross section, but can be any suitable shape as is known in the art. Further, the body component can be any suitable size and shape as is known in the art, depending on the wants and/or needs of a user.

In one embodiment, the body section of the body component comprises a textured surface or other gripping surface to ensure a user can easily grip and use the device.

In one embodiment, the open end of the body component is secured to an end component. The end component is tapered into a point, which allows a user to use the end component to scratch their scalp without ruining their hairstyle. The end component comprises opposing ends, a shaft, and a cylindrical shape. Specifically, the end component comprises a circular cross section and tapers from the shaft towards the distal end thereof. Further, the distal end, tapers into a point and preferably comprises a rounded distal tip in order to prevent injury or pain when applying pressure to a user's scalp while a user is scratching their scalp with the device.

In one embodiment, the body component and the end component are a single unitary structure.

In one embodiment, the body component and the end component are retractable, allowing the length of the body component and the end component to be expanded and/or retracted as necessary.

In one embodiment, the body component and the end component are solid throughout.

In one embodiment, the body component and the end component are hollow and comprise a chamber which can house oil, conditioners, moisturizers, water, etc., which are then dispelled through the end component, directly on the scalp.

In one embodiment, the body component comprises a button in communication with the chamber. The button can be positioned on any suitable location on the body component as is known in the art, and in a location that is convenient for a person to depress while holding the hair pick device in one hand. For example, the button may be disposed on the top surface of the body component or may be disposed on the side of the body component. In either location, the button may be depressed by the palm of the hand, by the thumb, or by a finger. Further, the button is movably carried on a flexible trigger.

In one embodiment, the trigger abuts the chamber. The trigger is resilient such that it flexes when the button is depressed. When the trigger flexes in response to the depression of the button, the trigger is urged against the chamber, such that it drives the liquid within the chamber towards the front of the chamber to be dispelled through the end component. The trigger may be manufactured from a resilient metal, such as spring steel. In other embodiments of the present invention, any of a variety of resilient materials may be used to form the trigger.

In one embodiment, the chamber comprises a delivery pipe and a pump disposed therein. Further, the body component comprises a removable lid on the closed end. The removable lid can be screwed on or snap fit, etc. The removable lid and pump seal liquid within the chamber, such that liquid may only exit the chamber through the pump and delivery pipe. Further, a dispensing nozzle is connected to the delivery pipe. The dispensing nozzle protrudes through the end component, such that liquid ejected from the dispensing nozzle is dispersed through and outwardly from the end component.

In one embodiment, the hair pick device is operated by depressing the button which drives the trigger into the chamber, causing the liquid within to move toward the delivery pipe and pump. The forward movement of the liquid drives the liquid against the pump causing liquid to be dispensed through the dispensing nozzle. The pump may be any of a variety of manual pumps known in the art that operate to dispense relatively small amounts of liquid with a short pump stroke. As such, an important aspect of the present invention is that the chamber is positioned relatively close to the dispensing nozzle. The chamber is thus positioned in the body component, so that the pump is close to the dispensing nozzle in the end component.

In one embodiment, the chamber comprises a valve in order to control the flow of liquid from the chamber to the dispensing nozzle. Any suitable valve can be used to selectively control the flow of liquid, such as a check valve. The valve is configured to open and close in order to release liquid from the chamber into the dispensing nozzle, as needed.

In one embodiment, the chamber can be filled with a liquid. Any liquid, such as water, lotions, oils, moisturizers, and/or hair conditioners, can be filled within the chamber and used to moisturize a user's scalp, as needed.

In one embodiment, when the chamber is empty, the removable lid may be removed and the chamber refilled or replaced with another chamber. In one embodiment, the chamber comprises a fill line, such that the chamber accommodates the movement of liquid without leaking, when in use.

In one embodiment, the body component comprises a motor that carries a weight off center, such that rapid rotation of the weight, causes the motor and thus the hair pick device to vibrate. The motor is powered by batteries which are secured within the body component. Further, a switch is provided, such that the motor may be selectively turned on or off. The switch may also allow the speed of the motor to be varied.

In yet another embodiment, the hair pick device comprises a plurality of indicia.

In yet another embodiment, a method of moisturizing and scratching a user's scalp while maintaining a desired hairstyle is disclosed. The method includes the steps of providing a hair pick device comprising a body component with a hollow chamber and an end component that tapers into a point. The method also comprises inserting the end component into a user's hair to scratch their scalp. Further, the method comprises dispensing moisturizers into the scalp, by pressing a button on the body component. Finally, the method comprises scratching and moisturizing a user's scalp while maintaining a desired hairstyle.

Numerous benefits and advantages of this invention will become apparent to those skilled in the art to which it pertains, upon reading and understanding the following detailed specification.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which:

FIG. 6 illustrates a flowchart showing the method of moisturizing and scratching a user's scalp while maintaining a desired hairstyle in accordance with the disclosed architecture.

DETAILED DESCRIPTION OF THE PRESENT INVENTION

Figure 1:
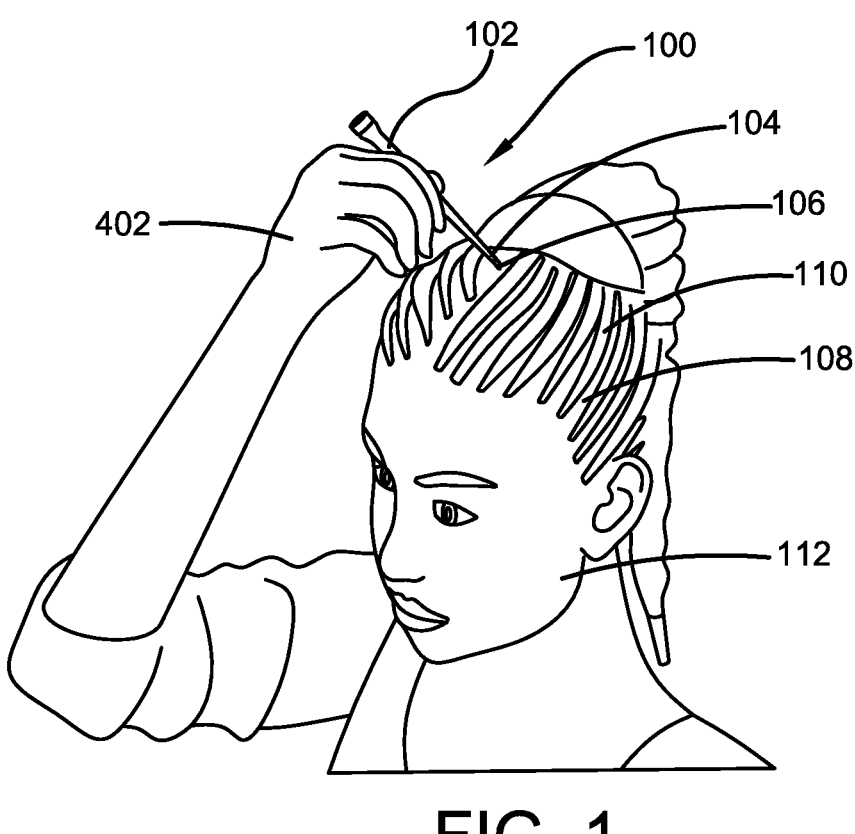
FIG. 1 illustrates a top perspective view of one embodiment of the hair pick device of the present invention showing a user scratching their scalp with the device in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long felt need in the art for a hair pick device that provides users with a pick-like tool for itching the scalp while wearing a wig, weave, dreadlocks, and other hairstyles. There is also a long felt need in the art for a hair pick device that allows users to itch the scalp without destroying the hairstyle and need to spend money at a salon to have it fixed. Further, there is a long felt need in the art for a hair pick device that features a hollow interior that can store moisturizer, allowing users to release the liquid through the tip via a small button on the pick. Moreover, there is a long felt need in the art for a device that enables users to both scratch itches and moisturize their scalp, all without ruining their hairstyle. Further, there is a long felt need in the art for a hair pick device that is retractable in length. Finally, there is a long felt need in the art for a hair pick device that comprises a solid shaft, without a chamber.

The present invention, in one exemplary embodiment, is a novel hair pick device. The device provides itch relief to a user's scalp while he/she is wearing different hairstyles, such as dreads, braids, weaves, and wigs, without ruining the hairstyle. The hair pick device comprises a body component that is configured in a cylindrical shape that may be solid or hollow. If hollow, the body component would also comprise a chamber, allowing the user to insert conditioners or other moisturizers into the device for application to the head. The conditions and moisturizers would be released via a button on the side of the body component. Further, the body component comprises an end component tapered into a point. The end component can be retractable or the device can be a single unitary piece. The present invention also includes a novel method of moisturizing and scratching a user's scalp while maintaining a desired hairstyle. The method includes the steps of providing a hair pick device comprising a body component with a hollow chamber and an end component that tapers into a point. The method also comprises inserting the end component into a user's hair to scratch their scalp. Further, the method comprises dispensing moisturizers into the scalp, by pressing a button on the body component. Finally, the method comprises scratching and moisturizing a user's scalp while maintaining a desired hairstyle.

Referring initially to the drawings, FIG. 1 illustrates a perspective view of one embodiment of the hair pick device 100 of the present invention. In the present embodiment, the hair pick device 100 is an improved hair pick device 100 that provides a user 112 with a pick-like tool for scratching the scalp 108 and providing itch relief while wearing a wig, weave, dreadlocks, and other hairstyles 110. The device 100 can maneuver through hairdos to scratch the scalp 108 without ruining the hairstyle 110. Specifically, the hair pick device 100 comprises a body component 102 with an end component 104 that tapers into a point 106 for scratching a scalp 108. Further, the body component 102 comprises a chamber 114 for dispensing moisturizing liquids 116. Thus, users 112 can scratch itches and moisturize their scalp 108 with the pick end component 104 without messing up their hairstyle 110.

Accordingly, the hair pick device 100 is adapted to be used as a pick to scratch a user's scalp 108 in order to conveniently and painlessly itch a user's scalp 108 without disturbing a user's hairstyle 110. This is especially useful when a user's hairstyle 110 includes braids, dreadlocks, weaves, wigs, etc., or any other suitable hairstyle as is known in the art.

Generally, the hair pick device 100 comprises a body component 102 manufactured from a suitable plastic, metal, wood, or other rigid material. The body component 102 comprises a closed end 118, an opposing open end 120, and a body section 122. The closed end 118, opposing open end 120 and body section (or shaft) 122 fit together tightly to form the body component 102. The body component 102 then has a substantially solid appearance that substantially approximates the appearance of a conventional hair pick. The body component 102 is substantially cylindrical in shape and comprises a circular cross section, but can be any suitable shape as is known in the art. Further, the body component 102 can be any suitable size and shape as is known in the art, depending on the wants and/or needs of a user 112.

Figure 2:
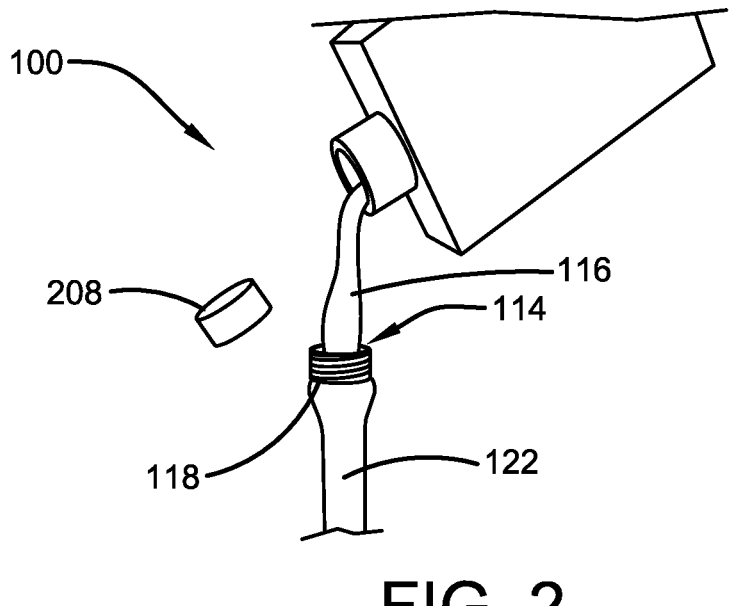
FIG. 2 illustrates a perspective view of one embodiment of the hair pick device of the present invention showing how oils and moisturizer are poured into the device in accordance with the disclosed architecture.
Figures 3A, 3B, 4A, 4B, 4C:
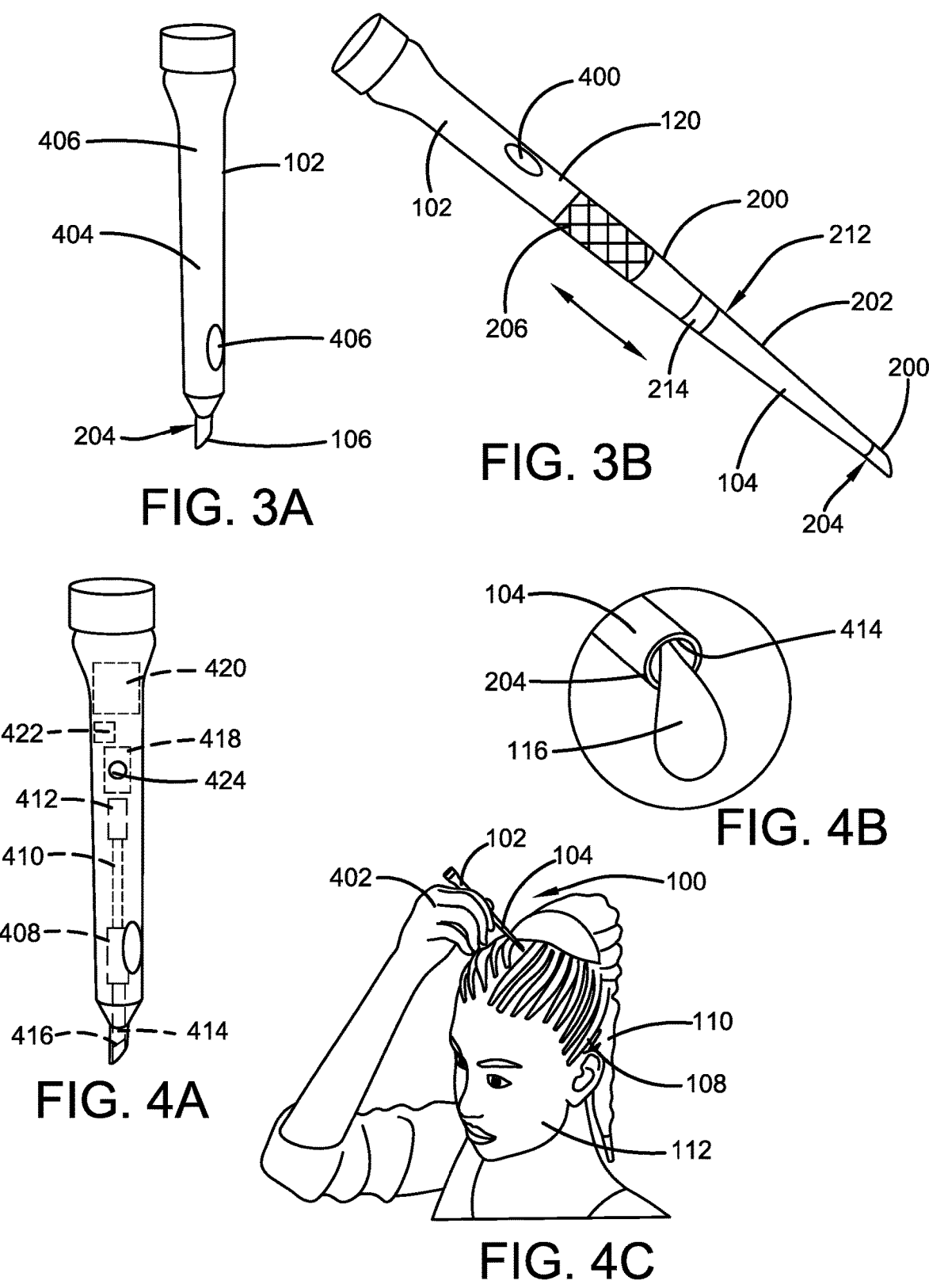
FIGS. 3A-B illustrate a perspective view of one embodiment of the hair pick device of the present invention showing how the body component is expanded and retracted in accordance with the disclosed architecture.
FIGS. 4A-C illustrate a top perspective view of one embodiment of the hair pick device of the present invention showing how moisturizer is dispensed via a button on the body component in accordance with the disclosed architecture.

As shown in FIGS. 2 and 3A-B, the open end 120 of the body component 102 is secured to an end component 104. The end component 104 is tapered into a point 106, which allows a user 112 to use the end component 104 to scratch their scalp 108 without ruining their hairstyle 110. The end component 104 comprises opposing ends 200, a shaft 202, and a cylindrical shape. Specifically, the end component 104 comprises a circular cross section and tapers from the shaft 202 towards the distal end 200 thereof. Further, the distal end 200, tapers into a point 106 and preferably comprises a rounded distal tip 204 in order to prevent injury or pain when applying pressure to a user's scalp 108 while a user 112 is scratching their scalp 108 with the device 100.

In one embodiment, the body component 102 and the end component 104 are a single unitary structure. In this same embodiment, the body component 102 and the end component 104 are solid throughout.

In another embodiment, the body component 102 and the end component 104 are retractable, allowing the length of the body component 102 and the end component 104 to be expanded and/or retracted as necessary. In this embodiment, the body component 102 and the end component 104 are telescoping and comprise at least one telescoping segment 212 that allows the total length of the device 100 to be extended or retracted. Each telescoping segment 212 is hollow and has a slip lock 214 for locking the segment 212 at a specific length. Further, the slip lock 214 is released by means of pressing or turning the slip lock 214.

Furthermore, the body section 122 of the body component 102 comprises a textured surface 206 or other gripping surface to ensure a user 112 can easily grip and use the device 100. The textured surface 206 can be any suitable texture, pattern, roughened area, etc., as is known in the art, depending on the needs and/or wants of a user 112.

In one embodiment, the body component 102 and the end component 104 are hollow and comprise a chamber 114 which can house liquids 116, such as oils, conditioners, moisturizers, water, etc., which are then dispelled through the end component 104, directly on the scalp 108.

Generally, the chamber 114 can be filled with a liquid 116. Any liquid 116, such as water, lotions, oils, moisturizers, and/or hair conditioners, can be filled within the chamber 114 and used to moisturize a user's scalp 108, as needed.

Furthermore, when the chamber 114 is empty, a removable lid 208 which secures the closed end 118 of the body component 102 may be removed and the chamber 114 refilled or replaced with another chamber 114, as needed. In one embodiment, the chamber 114 comprises a fill line 210, such that the chamber 114 accommodates the movement of liquid 116 without leaking, when in use.

As shown in FIGS. 4A-C, the body component 102 comprises a button 400 in communication with the chamber 114. The button 400 can be positioned on any suitable location on the body component 102 as is known in the art, and in a location that is convenient for a person to depress while holding the hair pick device 100 in one hand 402. For example, the button 400 may be disposed on the top surface 404 of the body component 102 or may be disposed on the side 406 of the body component 102. In either location, the button 400 may be depressed by the palm of the hand, by the thumb, or by a finger. Further, the button 400 is movably carried on a flexible trigger 408.

Generally, the trigger 408 abuts the chamber 114. The trigger 408 is resilient such that it flexes when the button 400 is depressed. When the trigger 408 flexes in response to the depression of the button 400, the trigger 408 is urged against the chamber 114, such that it drives the liquid 116 within the chamber 114 towards the front of the chamber 114 to be dispelled through the end component 104. The trigger 408 may be manufactured from a resilient metal, such as spring steel. In other embodiments of the present invention, any of a variety of resilient materials may be used to form the trigger 408.

Furthermore, the chamber 114 comprises a delivery pipe 410 and a pump 412 disposed therein. Further, the body component 102 comprises a removable lid 208 on the closed end 118. The removable lid 208 can be screwed on or snap fit, etc. The removable lid 208 and pump 412 seal liquid 116 within the chamber 114, such that liquid 116 may only exit the chamber 114 through the pump 412 and delivery pipe 410. Further, a dispensing nozzle 414 is connected to the delivery pipe 410. The dispensing nozzle 414 protrudes through the end component 104, such that liquid 116 ejected from the dispensing nozzle 414 is dispersed through and outwardly from the end component 104.

Accordingly, the hair pick device 100 is operated by depressing the button 400 which drives the trigger 408 into the chamber 114, causing the liquid 116 within to move toward the delivery pipe 410 and pump 412. The forward movement of the liquid 116 drives the liquid 116 against the pump 412 causing liquid 116 to be dispensed through the dispensing nozzle 414. The pump 412 may be any of a variety of manual pumps known in the art that operate to dispense relatively small amounts of liquid with a short pump stroke. As such, an important aspect of the present invention is that the chamber 114 is positioned relatively close to the dispensing nozzle 414. The chamber 114 is thus positioned in the body component 102, so that the pump 412 is close to the dispensing nozzle 414 in the end component 104.

In one embodiment, the chamber 114 comprises a valve 416 in order to control the flow of liquid 116 from the chamber 114 to the dispensing nozzle 414. Any suitable valve 416 can be used to selectively control the flow of liquid 116, such as a check valve. The valve 416 is configured to open and close in order to release liquid 116 from the chamber 114 into the dispensing nozzle 414, as needed.

In another embodiment, the body component 102 comprises a motor 418 that carries a weight 420 off center, such that rapid rotation of the weight 420, causes the motor 418 and thus the hair pick device 100 to vibrate. The motor 418 is powered by batteries 422 which are secured within the body component 102. Further, a switch 424 is provided, such that the motor 418 may be selectively turned on or off. The switch 424 may also allow the speed of the motor 418 to be varied.

Figure 5:
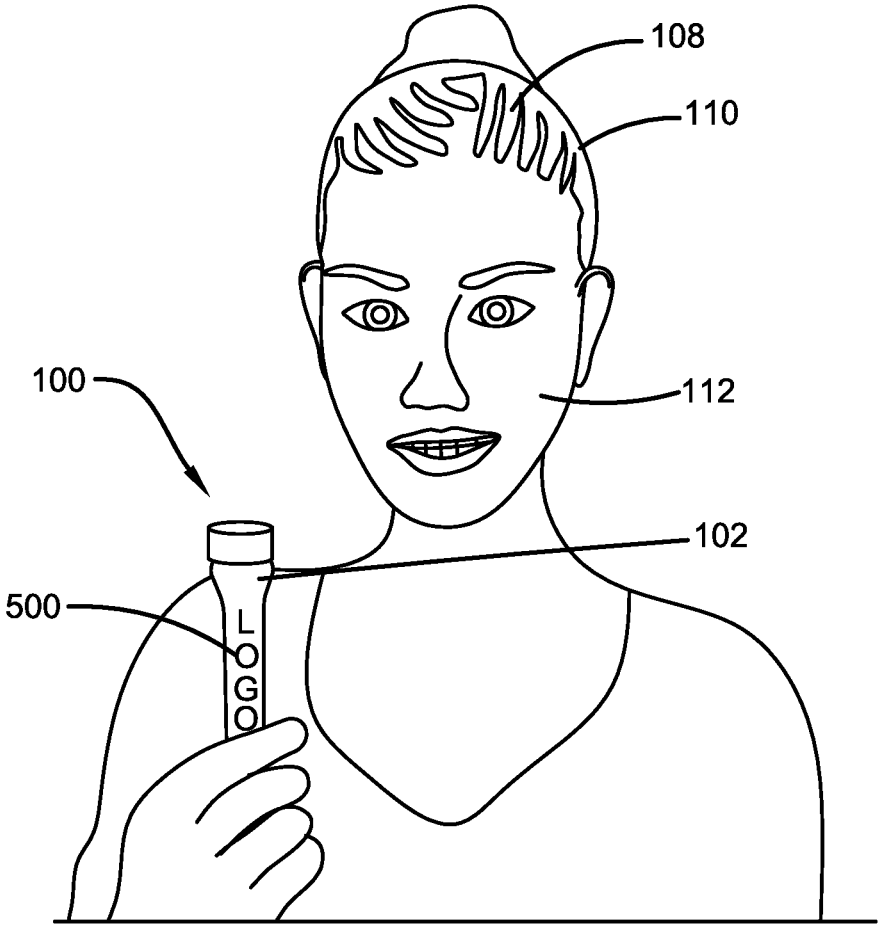
FIG. 5 illustrates a front perspective view of one embodiment of the hair pick device of the present invention in use in accordance with the disclosed architecture.

As shown in FIG. 5, the hair pick device 100 comprises a plurality of indicia 500. The body component 102 of the device 100 may include advertising, a trademark, or other letters, designs, or characters, printed, painted, stamped, or integrated into the body component 102, or any other indicia 500 as is known in the art. Specifically, any suitable indicia 500 as is known in the art can be included, such as but not limited to, patterns, logos, emblems, images, symbols, designs, letters, words, characters, animals, advertisements, brands, etc., that may or may not be hairstyle, moisturizing, or brand related.

FIG. 6 illustrates a flowchart of the method of moisturizing and scratching a user's scalp while maintaining a desired hairstyle. The method includes the steps of at 600, providing a hair pick device comprising a body component with a hollow chamber and an end component that tapers into a point. The method also comprises at 602, inserting the end component into a user's hair to scratch their scalp. Further, the method comprises at 604, dispensing moisturizers into the scalp, by pressing a button on the body component. Finally, the method comprises at 606, scratching and moisturizing a user's scalp while maintaining a desired hairstyle.

Certain terms are used throughout the following description and claims to refer to particular features or components. As one skilled in the art will appreciate, different users may refer to the same feature or component by different names. This document does not intend to distinguish between components or features that differ in name but not structure or function. As used herein "hair pick device", "hair device", "pick device", and "device" are interchangeable and refer to the hair pick device 100 of the present invention.

Notwithstanding the forgoing, the hair pick device 100 of the present invention can be of any suitable size and configuration as is known in the art without affecting the overall concept of the invention, provided that it accomplishes the above stated objectives. One of ordinary skill in the art will appreciate that the hair pick device 100 as shown in FIGS. 1-6 is for illustrative purposes only, and that many other sizes and shapes of the hair pick device 100 are well within the scope of the present disclosure. Although the dimensions of the hair pick device 100 are important design parameters for user convenience, the hair pick device 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A hair pick device that provides a user with a pick-like tool for scratching and moisturizing their scalp, the hair pick device comprising:
    a body component; and
    an end component; and
    wherein the body component and the end component are cylindrical in shape with a circular cross-section;
    wherein the body component is hollow and comprises a chamber for retaining a liquid which is dispensed on a scalp, as needed; and
    wherein the end component tapers into a point for scratching the scalp; and
    wherein the body component and the end component are retractable and comprise at least one telescoping segment that allows a total length of the hair pick device to be extended or retracted; and
    further wherein the at least one telescoping segment is hollow and has a slip lock for locking the at least one segment at a specific length.

2. The hair pick device of claim 1, wherein the hair pick device can be used to scratch a user's scalp without disturbing a user's hairstyle, which includes braids, dreadlocks, weaves, or wigs.

3. The hair pick device of claim 2, wherein the body component comprises a closed end, an opposing open end, and a body section, which fit together tightly to form the body component.

4. The hair pick device of claim 3, wherein the opposing open end of the body component is secured to the end component.

5. The hair pick device of claim 4, wherein the end component is tapered from shaft towards a distal end thereof, into a point which comprises a rounded distal tip in order to prevent injury or pain when applying pressure to a user's scalp.

6. The hair pick device of claim 1, wherein the body component and the end component are a single unitary structure.

7. The hair pick device of claim 3, wherein the body section of the body component comprises a textured surface for gripping.

8. The hair pick device of claim 1, wherein the liquid comprises oils, conditioners, moisturizers, or water, which is then dispelled through the end component, directly on the scalp.

9. The hair pick device of claim 8, wherein the closed end comprises a removable lid for refilling the chamber.

10. The hair pick device of claim 9, wherein the body component comprises a button in communication with the chamber for dispensing the liquid.

11. The hair pick device of claim 10, wherein the button is movably carried on a trigger which abuts the chamber and drives the liquid within the chamber to be dispelled through the end component.

12. The hair pick device of claim 11, wherein the chamber comprises a delivery pipe and a pump, such that the liquid may only exit the chamber through the pump and the delivery pipe and is dispensed through a dispensing nozzle connected to the delivery pipe.

13. A hair pick device that provides a user with a pick-like tool for scratching and moisturizing their scalp, the hair pick device comprising:
    a body component comprising a closed end, an opposing open end, and a body section, which fit together tightly to form the body component; and
    an end component secured to the opposing open end of the body component; and
    wherein the body component and the end component are cylindrical in shape with a circular cross-section;
    wherein the end component is tapered from shaft towards a distal end thereof, into a point which comprises a rounded distal tip in order to prevent injury or pain when applying pressure to a user's scalp;
    wherein the body component is hollow and comprises a chamber for retaining a liquid which is dispensed on a scalp, as needed;
    wherein the body component comprises a button in communication with the chamber for dispensing the liquid and a removable lid for refilling the chamber;
    wherein the button is movably carried on a trigger which abuts the chamber and drives the liquid within the chamber to be dispelled through the end component; and
    wherein the chamber comprises a delivery pipe and a pump, such that the liquid may only exit the chamber through the pump and the delivery pipe and is dispensed through a dispensing nozzle connected to the delivery pipe; and
    wherein the chamber comprises a valve in order to control the flow of the liquid from the chamber to the dispensing nozzle.

14. The hair pick device of claim 13, wherein the hair pick device is operated by depressing the button which drives the trigger into the chamber, causing the liquid within to move toward the delivery pipe and the pump to be dispensed through the dispensing nozzle.

15. The hair pick device of claim 13, wherein the body component comprises a motor that carries a weight off center, such that rapid rotation of the weight, causes the motor and thus the hair pick device to vibrate.

16. The hair pick device of claim 13 further comprising a plurality of indicia.

* * * * *